United States Patent [19]

De Munck et al.

[11] Patent Number: 5,091,599

[45] Date of Patent: Feb. 25, 1992

[54] COBALT HYDROFORMYLATION CATALYST RECOVERY IN THE PRODUCTION OF ALCOHOLS

[75] Inventors: Nicolaas A. De Munck, Barendrecht; Mattheus D. Olijve, Spykenisse, both of Netherlands

[73] Assignee: Exxon Chemical Patents Inc., Linden, N.J.

[21] Appl. No.: 504,234

[22] Filed: Apr. 4, 1990

[30] Foreign Application Priority Data

Apr. 4, 1989 [GB] United Kingdom ............... 8907577

[51] Int. Cl.$^5$ .................. C07C 29/16; C07C 45/50; B01J 31/40; B01J 38/68
[52] U.S. Cl. .................. 568/882; 568/451; 502/22; 502/24
[58] Field of Search .............. 502/22, 24; 423/139, 423/150; 568/451, 882

[56] References Cited

U.S. PATENT DOCUMENTS

| | | | |
|---|---|---|---|
| 2,751,403 | 6/1956 | Mertzweiller | 260/414 |
| 3,520,937 | 7/1970 | Moell et al. | 568/456 |
| 3,793,437 | 2/1974 | Takasu et al. | 423/417 |
| 3,941,848 | 3/1976 | Kummer et al. | 568/451 |
| 4,255,279 | 3/1981 | Spohn et al. | 502/24 |
| 4,400,299 | 8/1983 | Lagace et al. | 568/451 |
| 4,404,119 | 9/1983 | Lagace et al. | 502/28 |
| 4,625,067 | 11/1986 | Hanin | 568/451 |
| 4,647,707 | 3/1987 | Van Vliet | 568/882 |
| 4,658,068 | 4/1987 | Hanin | 568/883 |
| 4,982,011 | 1/1991 | Hanin | 568/628 |

FOREIGN PATENT DOCUMENTS

| | | |
|---|---|---|
| 0183545 | 6/1986 | European Pat. Off. |
| 1271911 | 7/1968 | Fed. Rep. of Germany |
| 2451473 | 10/1974 | Fed. Rep. of Germany |
| 48-17594 | 5/1973 | Japan |
| 1383658 | 2/1975 | United Kingdom |
| 1390398 | 4/1975 | United Kingdom |

OTHER PUBLICATIONS

R. Kummer et al., "New Hydroformylation Technology with Cobalt Carbonyls", Homogeneous Catalysis-II, Advances in Chemistry Series No. 132 (D. Forster et al.), pp. 19-26 (A.C.S. 1973).
R. B. King, Organometallic Synthesis, vol. 1, p. 98 (Academic Press, 1965).
W. Hieber and W. Hubel, Zeitschr. Elektrochem 57, No. 4, pp. 235-243 (1953).

Primary Examiner—Paul E. Konopka
Attorney, Agent, or Firm—J. J. Mahon

[57] ABSTRACT

Cobalt is recovered from the oil/water mixed reaction product of an oxonation reaction by converting the cobalt in the oil/water product to carbonyls and absorption of the carbonyls in the residue obtained from the upgrading of the heavy fraction of a hydroformylation reaction.

2 Claims, 2 Drawing Sheets

COBALT HYDROFORMYLATION CATALYST RECOVERY IN THE PRODUCTION OF ALCOHOLS

This invention relates to the production of alcohols and aldehydes by hydroformylation processes and in particular the production of alcohols and aldehydes by cobalt catalysed hydroformylation in which the cobalt recovery from the product of hydroformylation is improved. This brings an economic benefit and reduces the amount of cobalt in the waste stream leading to significant environmental benefits.

The hydroformylation process, in general terms, is a process involving the preparation of oxygenated organic compounds by the reaction of carbon monoxide and hydrogen (synthesis gas) with carbon compounds containing olefinic unsaturation. The reaction is performed under hydroformylation conditions in the presence of a carbonylation catalyst or catalyst precursor typically a cobalt catalyst such as dicobalt octacarbonyl, and results in the formation of a compound, e.g., an aldehyde which has one more carbon atom in its molecular structure than the feedstock. Subsequent hydrogenation of the primary product leads to alcohols.

Hydroformylation may be used to produce lower alcohols such as propanol, butanol, isoamyl alcohol, isohexyl alcohol and isoheptyl alcohol in which the feedstock for the hydroformylation process typically is a commercial $C_2$–$C_6$ olefin fraction and the desired end product is the respective $C_3$–$C_7$ saturated alcohol or derived mixed alcohol product, produced by hydrogenation of the aldehyde oxonation product. For lower alcohols the feedstock may be ethylene, propylene, butene, or amylene.

By virtue of the nature of the feedstock commonly available to industry, and indeed of the catalyst and reaction parameters employed, the oxonation reaction yields a range of products due to the numerous secondary reactions which take place.

The main commercial products of the hydroformylation reaction are aldehydes and alcohols, with side reactions in the oxonation, demetalling and hydrogenation sections of the process system producing some 5 to 20 wt. % of high boiling materials by condensation, esterification and dehydration reactions.

In a conventional higher oxo alcohol process, the feedstock is fed together with synthesis gas into an oxonation unit where catalytic hydroformylation takes place using, e.g., hydro cobaltcarbonyl as the active catalyst species.

After oxonation the product goes through a hydrogenation step to convert aldehydes into alcohols. Prior to the hydrogenation step the crude oxo reaction effluent which contains dissolved cobalt catalysts, the aldehyde and alcohol products and reaction byproducts together with any metallic contaminants is generally treated to remove the dissolved cobalt catalyst so that, for reasons of economy it may then be recycled to the oxonation reactor.

The present invention is concerned with an improvement in the recovery of the dissolved cobalt.

In the higher alcohol process the product mixture after hydrogenation comprising the higher alcohol, the high boiling materials mentioned above and a low boiling fraction is passed to a distillation unit where low boiling materials, high boiling materials and the desired alcohol product are separated.

The low boiling material passing off overhead is a low value product, typically containing unreacted olefin feed and paraffins. The high boiling material usually contains dimers such as ethers and ether-alcohols, (e.g., $C_{20}$ compounds in $C_{10}$ alcohol production) and trimers such as acetals, (e.g., $C_{30}$ compounds in $C_{10}$ alcohol production), and heavier compounds.

Although this heavier fraction is substantially alcohol free (apart from the heavy ether alcohols), it may contain a minor amount of alcohol which has not been removed in the distillation stage where the higher alcohol product of the hydroformylation process is separated. In our European patent publication 0183545 we describe a process for upgrading these heavy fractions to more useful alcohol.

A wide variety of catalyst recovery/recycle processes have been developed. U.S. Pat. No. 2,751,403 for example is directed to a process in which cobalt is removed from crude oxo products by extraction with an aqueous acid such as acetic acid to form an aqueous extract containing cobalt in both the cationic and anionic forms, viz, as the anion $[Co(CO)_4^-]$ and the corresponding cobalt salt, cobaltous bis-tetracarbonylcobaltate $Co^{++}[Co(CO)_4^-]_2$. The aqueous extract is then subjected to oxidation with air or oxygen at 38° to 66° C. and at a pH of 5-6 with the addition of a higher molecular weight carboxylic acid salt e.g. sodium oleate, to convert anionic cobalt to the $Co_{++}$ form and to achieve substantially quantitive recovery of the cobalt as a cobalt soap e.g. cobaltous oleate which was the desired catalytic species. The cobalt soap is then extracted into an organic liquid for recycle to the oxo reactor.

However, there has been continuous interest in other, low cost alternatives to such expensive cobalt soaps, which during use are converted to other forms and have to be reconverted to the soap during the recycle process.

In U.S. Pat. No. 3,793,437 crude oxo effluent containing cobalt is contacted with an aqueous solution of metallic extracting agents, such as various metal salts and certain zeolites, in the presence of $H_2$ and CO to form an aqueous salt of carbonyl cobaltate which is subsequently decomposed with an organic acid or a mineral acid to a water-soluble cobalt hydridocarbonyl. The aqueous solution containing the cobalt hydridocarbonyl is then heated in the presence of CO and a water-immiscible organic solvent to form dicobalt octacarbonyl which is extracted into the organic solvent. After further treatment (e.g., drying, dilution or concentration), the organic solvent can be recycled to the oxo reactor. The patentees indicate that the thus-recovered cobalt carbonyl is sensitive to oxygen or oxidizing agents and must be protected from such oxidants as by degassing or by replacement of the ambient atmosphere with inert gas.

R. Kummer, et al., "New Hydroformylation Technology with Cobalt Carbonyls" Homogeneous Catalysis-II, Advances in Chemistry Series No. 132 (D. Forster et al), pp. 19-26 9 (A.C.S. 1973) relates to a BASF process in which crude oxo product is demetalled at 120° C., and 10 atm, with air and an aqueous formic acid/cobaltous formate solution, and the resulting aqueous $Co^{++}$ formate solution is reacted with CO and $H_2$ to perform anionic cobalt, $Co(CO)_4^-$, in the solution, which is then subjected to an olefin extraction to give an olefin phase containing cobalt as either $Co_2(CO)_8$ or (at low CO pressure) $Co_4(CO)_{12}$. Kummer et al describes the crude oxo product demetalling step by the following equation (I):

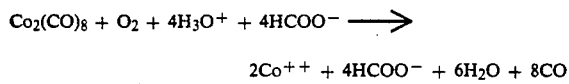

$$2Co^{++} + 4HCOO^- + 6H_2O + 8CO$$

The authors point out that the resulting aqueous phase contains all the cobalt and that only water-soluble $Co^{++}$ compounds are formed.

German Patent 1,272,911 to BASF, as cited at 69 Chem. Abs. 95964d (1968), describes the demetalling of a crude oxo product at 116° C. and 30 atm. with air, acetic acid, water and a recycled $Co^{++}$ salt solution, using a residence time in the demetalling zone of 3 seconds, to give an organic phase containing practically no cobalt.

U.S Pat. No. 3,941,848; British Patent Nos. 1,383,658 and 1,390,898; and German Offenlegungschrift. No. 2,451,473 (1976) relate to similar processes.

U.S. Pat. No. 4,255,279 contacts a crude oxo effluent in a first step with an aqueous $Co^{++}$ salt of an organic or inorganic acid to extract cobalt into the aqueous phase. After separation from the thus-treated crude oxo product, the aqueous phase, which contains cationic and anionic cobalt $Co^{++}$ and $Co(CO)_4^-$, is treated with syn gas to perform additional $Co^{++}$ into the anionic, $Co(CO)_4^-$, form. The preformed effluent is then contacted with an organic phase for ultimate recycle to the oxo reactor.

The treated crude oxo product obtained from the first step still contains some cobalt in an oil-soluble form e.g., dicobalt octacarbonyl, and is further demetalled by treatment at 65° to 93° C., with an aqueous organic or inorganic acid and oxygen to oxidize the cobalt to a water-soluble form, e.g., $Co^{++}$ salt of the selected acid. The patentees indicate that substantially all of the cobalt is thereby separated from the organic layer, resulting in an oxo product containing cobalt in a concentration of about 10 ppm or less.

Japanese Patent Publication No. 73/17,594 (May 30, 1973) oxidizes a cobalt hydrocarbonyl water-soluble metal salt (e.g., $NaCo(CO)_4$ or $Co[Co(CO)_4]_2$) in aqueous solution with air or $O_2$ to form dicobalt octacarbonyl solids, followed by extraction thereof using an organic solvent or raw material olefin or their mixture.

In R. B. King, Organometallic Synthesis Vol. 1 p. 98 (Academic Press 1965), it is indicated that $Co_2(CO)_8$ crystals are soluble in organic solvents; are unstable to both thermal decomposition and air oxidation; and rapidly lose CO at 50° C. to form $Co_4(CO)_{12}$ and ultimately cobalt metal. On exposure to air for several minutes $Co_2(CO)_8$ crystals are said to be oxidised to a $Co^{++}$ derivative, which is presumed to be either the oxide or the carbonate. Also, $Co_2(CO)_8$ crystals, when isolated by crystallization from organic solvents, are said to be pyrophoric if obtained as finely divided crystals. A preparatory procedure is therefore suggested in which cobalt (II) acetate tetrahydrate is reacted at 160°–180° C. with CO and $H_2$ to form acetic acid and $Co_2(CO)_8$ crystals, which are isolated by filtration under $N_2$.

W. Hieber and W. Hubel, Zeitschr. Elektrochem 0.57, no. 4; pp 235–243 (1953) indicate that solutions of cobalt carbonyl hydride are very sensitive to oxidizing agents and that dimeric cobalt carbonyl flakes are immediately formed from even minute traces of atmospheric oxygen (see Section I, paragraph 2).

U.S. Pat. No. 4,404,119 describes a technique in which crude oxo product is first treated with an aqueous phase containing a $Co^{++}$ salt, the aqueous and organic phases are separated, the aqueous phase containing the cobalt salt of the acid is then treated with syngas to form cobalt carbonyl which are then oxidised and extracted. Olefins or the hydroformylation product including the heavy oxygenated product (HOF) are mentioned as suitable extractants.

In another process the cobalt catalyst is oxidised with air/acetic acid to form cobalt acetate followed by thermal decobalting to form cobalt metal, or treatment of the cobalt catalyst with dilute caustic to product sodium cobaltcarbonyl, the latter is known as the Kuhlmann catalyst cycle technology and involves two main process steps: first recovery of the sodium cobaltcarbonyl and second the regeneration of the hydro cobaltcarbonyl.

The first step of this Kuhlmann Cycle consists of high pressure decobalting in which oil soluble hydro cobaltcarbonyl is converted into the water soluble sodium cobaltcarbonyl. This is typically done at high temperature (100°–180° C.) and high pressure 180–300 barg) by thoroughly mixing the oxonation products with a dilute caustic solution.

After cooling and depressuring the sodium cobaltcarbonyl water is separated from the oil, and after washing the oil with water for removal of cobalt traces, both water phases are combined and stored.

In the second step, the water soluble sodium cobaltcarbonyl is converted back into the oxonation catalyst hydro cobaltcarbonyl by acidification of the cobalt water with dilute sulphuric acid. The volatile hydro cobaltcarbonyl is stripped from the water by a countercurrent flow of absorbing gas, frequently syngas, which is subsequently passed through an absorber column to recover the hydro cobaltcarbonyl from the stripping gas.

We have now found that the residual product after the upgrading of the heavy fraction obtained in the oxonation process as is, for example, described in European Patent Publication 0183545 is particularly useful for the extraction of cobalt. We find this to be particularly useful in the conversion of lower olefins such as propylene, butenes, pentenes and hexenes where extraction of the olefins themselves is more difficult due to their volatility leading to product losses and olefin are too volatile to act as catalyst absorption agents. This is particularly so when the olefin streams also contain paraffins.

The present invention therefore provides a process for the recovery of cobalt from the oil/water mixed reaction product of an oxonation reaction by converting the cobalt in the oil/water product to carbonyls and absorption of the carbonyls in the residue obtained from the upgrading of the heavy fraction obtained during hydroformylation.

The process is applicable to the production of alcohols from any olefins which may be subjected to hydroformylation, but is particularly suited to the hydroformylation of $C_3$ to $C_6$ olefins for the production of $C_4$ to $C_7$ alcohols.

Conventional hydroformylation conditions may be used in the process of this invention and the operating temperatures, pressures and other conditions, such as synthesis gas composition, may be controlled in accordance with the usual expertise of the person skilled in the art to maximise yield of the desired alcohol. For example, the hydroformylation reaction may be carried out at a pressure of 150–300 atm, and a temperature of from 120°–190° C.

The catalyst may be used in desired active form for example in a concentration of from 0.05–3 wt. % preferably 0.05 and 1 wt. % as metal based on the olefinic feed. Typically the synthesis gas used might have a $H_2:CO$ volume ratio in the range 0.9:1–1.5:1.

Figure 1:
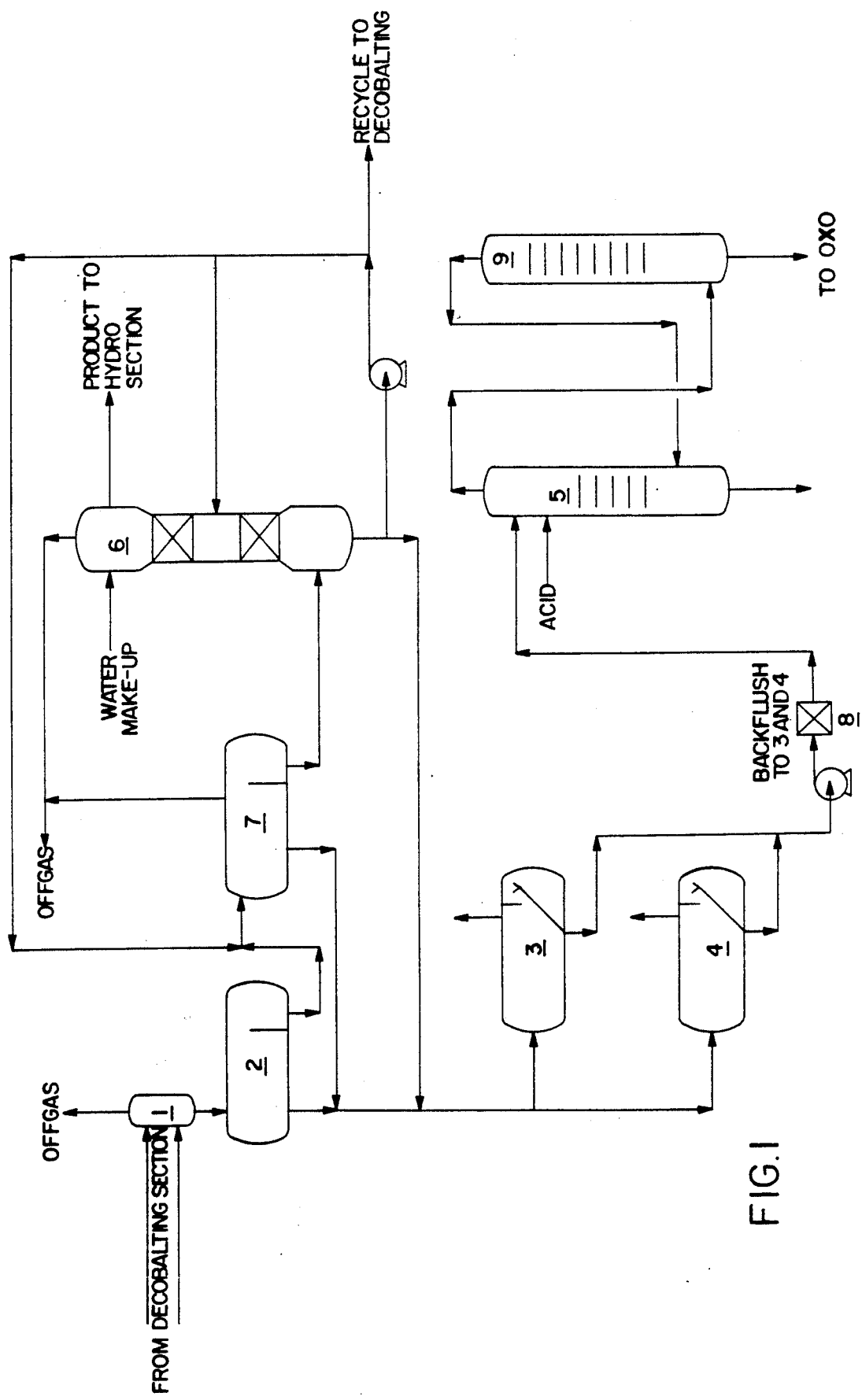
FIG. 1 shows the application of the invention to a process for hydroformylation and FIG. 2 illustrates the equipment used to carry out the tests described in the Examples.

The present invention is illustrated by the accompanying diagramatic FIG. 1, in which oxo product and dilute caustic containing sodium cobaltcarbonyl come from the decobalting section and flow into low pressure gas-liquid separator 1. The liquids from separator 1 flow into water-oxo product separator 2. The separated oxo product is mixed with recycled wash water from tower 6 and sent to a second water-oxo product separator 7.

The oxo product from separator 7 is fed to wash tower 6, while the water phase is combined with the one from separator 2 and sent to settlers 3 and 4.

In wash tower 6 the oxo product is water washed and after separation sent to hydrogenation. The wash water from tower 6 bottoms is partly recycled over tower 6 itself, partly sent to separator 7, while the remaining goes to settlers 3 and 4.

In settlers 3 and 4 entrained oxo product and solids are separated from the sodium cobalt carbonyl water, which is pumped through cobalt solids filter 8 to stripper column 5. The cobalt solids which build up in filter 8 are regularly back flushed into settlers 3 and 4.

In stripper column 5 acid is added to the sodium cobaltcarbonyl water and is countercurrently stripped with gas. This stripgas containing hydro cobaltcarbonyl is contacted in absorber 9 with an absorbent to recycle the cobalt catalyst back to oxonation, traditionally the absorbent is oxo feed whereas in this invention it is the residue obtained from the upgrading of the heavy fraction obtained during hydroformylation. The stripped water from column 5 is sent to conventional end-of-pipe treatment or to a sewer.

Traditionally, the heavy byproducts formed during oxonation are used for this purpose. Unfortunately, these heavy byproducts are an inferior hydro cobaltcarbonyl absorbent compared to olefin feed. They are not capable of fully absorbing the hydro cobaltcarbonyl, which causes hydro cobaltcarbonyl losses into the purge gas stream leaving the absorber tower. To partly solve this problem the purge gas is then passed through a second scrubber tower to minimize cobalt losses in the offgas. A poor stripping performance in the stripper tower is caused by the recirculation of the scrubbed gas with hydro cobaltcarbonyls from the absorber back to the stripper tower. This leaves a lot of unstripped cobalt in the acidified waste water, which either goes into the environment or requires additional cleanup steps.

We now have discovered that so called U.HOF, the product left after upgrading of the heavy oxo byproducts is a very effective hydro cobaltcarbonyl absorption fluid, almost comparable to olefin feed and much better than the heavy oxo byproducts themselves (known as virgin HOF-V.HOF). U.HOF is the heavy product derived after subjecting the heavy oxo byproducts to cracking which may be achieved by subjecting the byproduct to a temperature in the range 300°–350° C., at low pressure and in the presence of steam and a catalyst, such as-alumina as is described in European Patent application EP 183,545. The products of the catalytic cracking reaction are condensed and separated into a light fraction containing aldehydes/alcohol and a heavy fraction named U.HOF which according to this invention is used for the extraction of cobalt from the oil/water product of the oxonation reaction.

We find that the use of U.HOF as a hydro cobaltcarbonyl absorbent is particularly useful in the conversion of butenes and pentenes into amyl and hexyl alcohols where there are currently high cobalt losses (with heavy oxo byproduct) or high hydrocarbon losses and poor operability (with olefin feed).

Whilst it is possible to use hexenes as an absorbent for hydrocobaltcarbonyl provided the hexene contains little light ends and the absorber tower is operated at low temperature (15° C.). However, at higher operating temperatures (over 20° C.) caused by "warm" cooling water in the summer and autumn the hexenes become too volatile. This will also happen when the hexenes are rich in $C_5$ olefins/paraffins. In both cases the hexenes will vaporize in the absorber and condense in the stripper and cause hydrocarbon losses. The use of U.HOF overcomes this problem.

Figure 2:
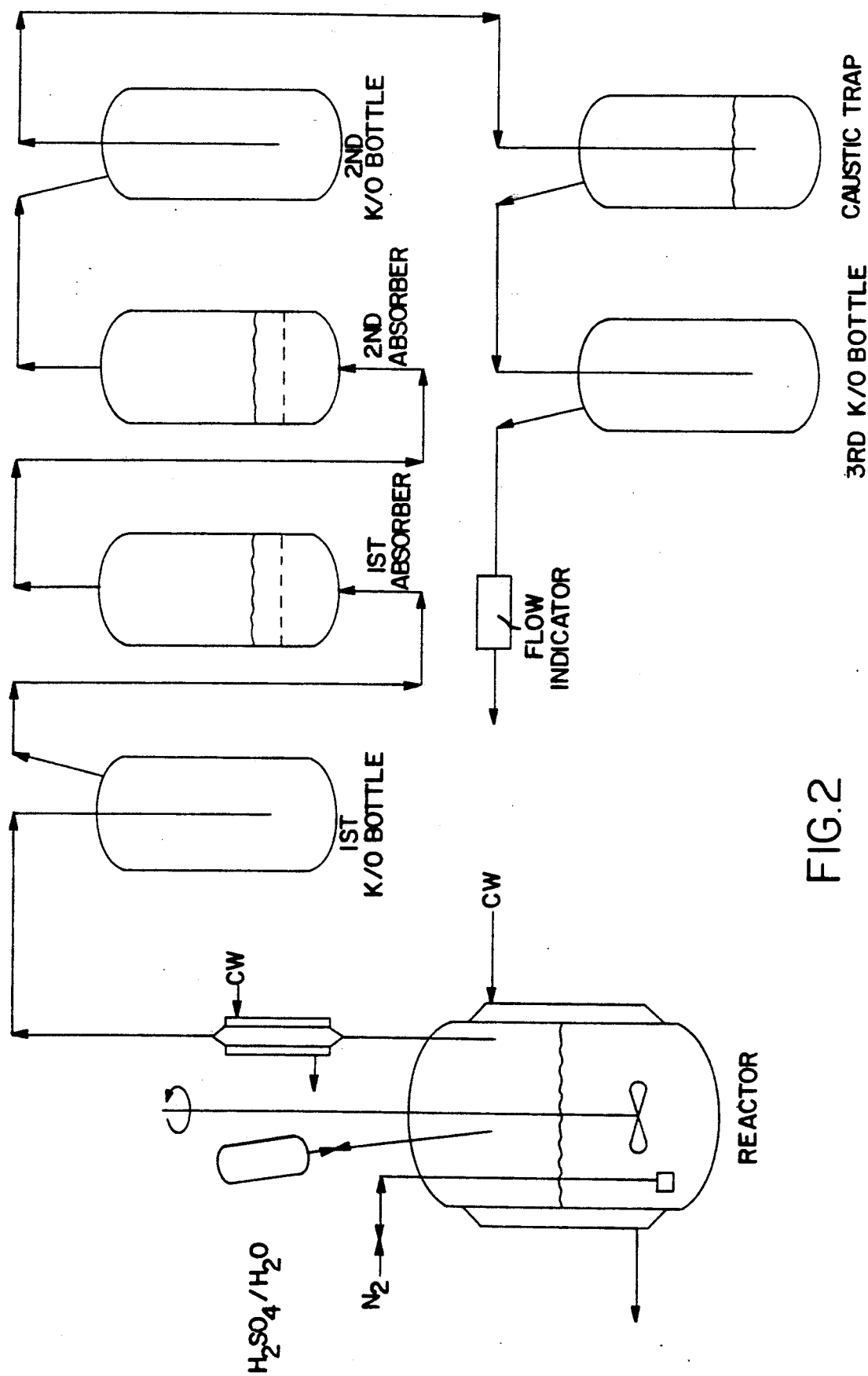

In the following examples the ability of various materials to absorb cobalt was tested in the equipment illustrated in FIG. 2 which consists of a five liter/glass stirred reactor equipped with a jacket for cooling/heating, a nitrogen sparger, a reflux condenser, and a vessel for injection of diluted sulphuric acid has been used. The nitrogen stripgas goes via a knockout bottle to two absorbers with fritted gas for distribution having a volume of 200 ml. After passing another knockout bottle the remaining cobaltcarbonyls are caught in a caustic trap. The gas goes finally to a dry gas meter to get a flow indication.

EXAMPLE 1

Sodium cobaltcarbonyl ($NaCo(CO)_4$) solution in water containing 14000 ppm cobalt is slowly acidified by addition of 16 wt. % sulphuric acid in a stirred tank reactor to obtain a final sulphuric acid concentration of 3 wt. % excess.

Due to the acidification hydro cobaltcarbonyl is formed, which is stripped with $N_2$ and the gas is led through two absorbers in series which contain the test solvents. The remaining cobalt which is not absorbed, is recovered in a caustic trap (10 wt. %). Three knock-out bottles were installed to prevent contamination of the different liquids due to entrainment.

The batch $NaCo(CO)_4$ solution was stripped for 15 min., while stirring the liquid. The gasflow was in the range of 1–2 liters/min., a more accurate flow measurement was not possible due to the low gas rate.

At the end of the test the solutions were weighted and the cobalt concentrations determined by titration using a standard EDTA method.

From these data a cobalt balance was calculated and the results are given in Table 1.

Nonene was taken as a basis for comparison, while $C_{10}$ virgin HOF (V.HOF), $C_{10}$ U.HOF, and blends of $C_{10}$ U.HOF with hexene or iso-heptyl alcohol were tested for cobalt loading potential. Cobalt balance closure was checked, poor balances were caused by the formation of cobalt metal during volatilization and by absorption of cobalt carbonyl into the rubber hose material and on the glass.

At breakthrough conditions, as indicated by cobalt buildup in the caustic trap, the nonene cobalt loading was 3.5 wt. %. Under similar conditions decyl alcohol U.HOF absorbed 2.4-2.7 wt. % Co. The performance of decyl alcohol Virgin.HOF was significantly worse, with 2.0 wt. % cobalt in the first absorber a breakthrough occurred into the second absorber and the caustic trap.

During the experiments it was observed that Virgin.HOF was much more viscous than U.HOF, and it had more tendency to foaming. Furthermore use of Virgin.HOF will cause a yield debit over the use of U.HOF. The much better performance of U.HOF than V.HOF is believed to be related to the olefinic nature of U.HOF, batch oxonations of U.HOF have demonstrated that U.HOF is converted to aldehyde containing material, while V.HOF is more or less inert.

Some additional experiments were carried out to screen the effect of addition of hexene or isoheptyl alcohol to the U.HOF. Results are also listed in Table 1. Although not tested at cobalt breakthrough conditions extrapolation of the results of tests 5-7 compared with the results of tests 2-3 show no significant effect of adding hexene or isoheptyl alcohol to the U.HOF.

The results show, that decyl alcohol U.HOF is a good solvent for hydro cobaltcarbonyl. The $C_{10}$ U.HOF will be formed as blend with the heavy components ($C_{14}/C_{15}$) which are also formed.

TABLE 1

| SOLVENT | ppm Cobalt 1st Absorber | ppm Cobalt 2nd Absorber | ppm Cobalt Caustic Trap | Cobalt Balance % |
|---|---|---|---|---|
| 1. Nonene | 36086 | 8732 | 2159 | 93.8% |
| 2. U.HOF ($C_{10}$) | 26962 | 7968 | 1674 | 73.0% |
| 3. U.HOF ($C_{10}$) duplicate test | 24456 | 8735 | 2588 | 83.5% |
| 4. V.HOF ($C_{10}$) | 19915 | 13139 | 6359 | 79.4% |
| 5. U.HOF ($C_{10}$) + 10% Hexene | 18184 | 4878 | 110 | 68.5% |
| 6. U.HOF ($C_{10}$) + 10% Hexene | 13373 | 1626 | 36 | 68.9% |
| 7. U.HOF ($C_{10}$) + 10% IHA | 14955 | 1527 | 116 | 62.5% |

• Absorption test carried out at ambient temperature (20° C.)

The following Examples illustrate the recovery of cobalt catalyst from the product of the production of isoheptyl alcohol by standard cobalt catalysed hydroformylation in which a mixture of 15 wt. % cracked heavy oxo byproducts and 85 wt. % hexenes are contacted with synthesis gas having a $H_2/CO$ ratio of 1.4-1.5 at 165° and 250-270 bar operating pressure with cobalt concentrations in the order of 0.07-0.1 wt. %.

EXAMPLE 2

The beneficial effect of using U.HOF as a cobaltcarbonyl catalyst absorption agent is illustrated in the following examples with reference to FIG. 1.

Water containing sodium cobaltcarbonyl is fed to tower 5 at a rate of 3.5 tn/hr and at a temperature of 25° C.

The stripped product leaving tower 5 typically contained 53 ppm of cobalt and had an acidity of 3.1 wt. % due to excess sulfuric acid.

The stripping gas containing hydro cobaltcarbonyl is fed into tower 9 and contacted with a countercurrent flow of U.HOF. At a rate of 2.0 tn/hr the U.HOF contained 4510 ppm cobalt, whereas the scrubbed stripping gas had a cobalt concentration of less than 2000 mg/m$^3$. The temperature of the absorption tower was 13° during this test.

The bottom product from tower 9 containing hydro cobaltcarbonyl is mixed with hexenes and fed to the oxonation section in which the hexenes are converted into isheptyl alcohol.

COMPARATIVE EXAMPLE 3

Water containing sodium cobaltcarbonyl is fed to tower 5 at a rate of 3.8 tn/hr and at a temperature of 25° C.

The stripped product leaving tower 5 contained 50 ppm of cobalt, but had an acidity of 4.5 wt. % excess sulfuric acid to facilitate the stripping of the hydro cobaltcarbonyl from the water.

The stripping gas containing hydro cobaltcarbonyl is fed into tower 9 and contacted with a countercurrent flow of V.HOF. At a rate of 3.0 tn/hr the V.HOF contained 2721 ppm cobalt.

The scrubbed stripping gas had a cobalt concentration of 2440 mg/m$^3$.

The temperature of the absorption tower was 15° C.

This comparative example illustrates that the use of V.HOF requires a higher acid content in the water from tower 5, while at the same time a higher V.HOF flow to tower 9 is required to produce a scrubbed gas still containing a higher cobalt content than obtained with the use of U.HOF in tower 9.

COMPARATIVE EXAMPLE 4

Water containing sodium cobaltcarbonyl is fed to tower 5 at a rate of 4.2 tn/hr and at a temperature of 30° C.

The stripped product leaving tower 5 contained 49 ppm of cobalt with an acidity of 3.6 wt. % excess sulfuric acid.

The stripping gas containing hydro cobaltcarbonyl is fed into tower 9 and contacted with a countercurent flow of V.HOF.

At a rate of 4.2 tn/hr the V.HOF absorbed 2360 ppm cobalt, whereas the scrubbed stripping gas contained 2404 mg/m$^3$ cobalt.

The temperature of the absorption tower was kept at 14° C.

This example again illustrates that V.HOF is less effective cobaltcarbonyl absorption agent as compared to U.HOF.

Despite running at a double flow rate over tower 9 the stripping gas nevertheless has a higher cobalt content.

Furthermore a higher sulfuric acid rate to tower 5 is necessary to free the water from cobaltcarbonyls, despite increasing the temperature from 25° C. to 30° C.

We claim:

1. In the method of hydroformylating $C_3$ to $C_6$ olefins to produce $C_4$ to $C_7$ alcohols, said hydroformylation being carried out at a pressure of 150-300 atm and a temperature of from 120°-190° C. in the presence of a cobalt hydroformylation catalyst comprising hydro cobalt carbonyl at a catalyst concentration of from 0.05-3 wt. %, based on the olefins, and in which hydroformylation process the crude product is treated with a dilute caustic solution to provide a water phase which is separated from the crude hydroformylation product, the water phase containing sodium cobalt carbonyl is acidified and gas stripped to provide hydro cobalt carbonyl, and said crude hydroformylation product is hydrogenated to provide a mixture comprising materials and separating therefrom the low boiling materials and alcohol to obtain a heavy fraction containing dimers and trimers and catalytically cracking said fraction at a temperature in the range of 300°–350° C. in the presence of steam and an alumina catalyst to provide a light fraction and a heavy fraction (U. HOF), the improvement which comprises recovering said U. HOF and recycling said U. HOF and using said U. HOF as an absorbent for the hydro cobalt carbonyl catalyst which is recycled back to the hydroformylation reactor.

2. The process of claim 1 wherein the olefin is butene or pentene.

* * * * *